(12) United States Patent
Sánchez Casals et al.

(10) Patent No.: US 8,163,924 B2
(45) Date of Patent: Apr. 24, 2012

(54) PROCESS FOR PREPARING A LEUKOTRIENE ANTAGONIST AND AN INTERMEDIATE THEREOF

(75) Inventors: Carles Sánchez Casals, Rubí (ES); Helena Camps Ramírez De Cartagena, Rubí (ES)

(73) Assignee: Moehs Ibérica, S.L., Rubi (ES)

( * ) Notice: Subject to any disclaimer, the term of this patent is extended or adjusted under 35 U.S.C. 154(b) by 106 days.

(21) Appl. No.: 12/670,530

(22) PCT Filed: Jul. 30, 2008

(86) PCT No.: PCT/EP2008/059965
§ 371 (c)(1),
(2), (4) Date: Jan. 25, 2010

(87) PCT Pub. No.: WO2009/016191
PCT Pub. Date: Feb. 5, 2009

(65) Prior Publication Data
US 2010/0204476 A1   Aug. 12, 2010

(30) Foreign Application Priority Data

Jul. 31, 2007   (ES) .................................. 200702220

(51) Int. Cl.
*C07D 215/18*   (2006.01)
(52) U.S. Cl. ....................................................... 546/174
(58) Field of Classification Search .................. None
See application file for complete search history.

(56) References Cited

U.S. PATENT DOCUMENTS

2005/0107612 A1*   5/2005   Reguri et al. ................. 546/177

FOREIGN PATENT DOCUMENTS

| EP | 0 480 717 A1 | 4/1992 |
|---|---|---|
| EP | 0 500 360 A1 | 8/1992 |
| EP | 0 737 186 A1 | 10/1996 |
| WO | WO 2006/008751 A2 | 1/2006 |
| WO | WO 2007/004237 A2 | 1/2007 |
| WO | WO 2007/057225 A2 | 5/2007 |
| WO | WO 2008/320991 A2 | 3/2008 |

OTHER PUBLICATIONS

Vippagunta et al., Crystalline solids, 48 Adv. Drug Delivery Rev. 3-26 (2001).*
King et al., 58 J. Org. Chem. 3731-3735 (1993).*

* cited by examiner

*Primary Examiner* — Janet Andres
*Assistant Examiner* — Timothy R Rozof
(74) *Attorney, Agent, or Firm* — ProPat, L.L.C.

(57) ABSTRACT

Dicyclohexylamine salt of formula (IIa) or a pharmaceutically acceptable solvate thereof, including a hydrate, and its process for preparation are provided. The invention also relates to processes for the preparation of montelukast of formula (I) or a pharmaceutically acceptable salt thereof, or a pharmaceutically acceptable solvate thereof, including a hydrate, based on the conversion of a salt of formula (IIa) into its form of free acid, followed by reaction with a compound of formula (III) CH3MgX, wherein X is halogen, in a suitable solvent, optionally in the presence of a Lewis acid.

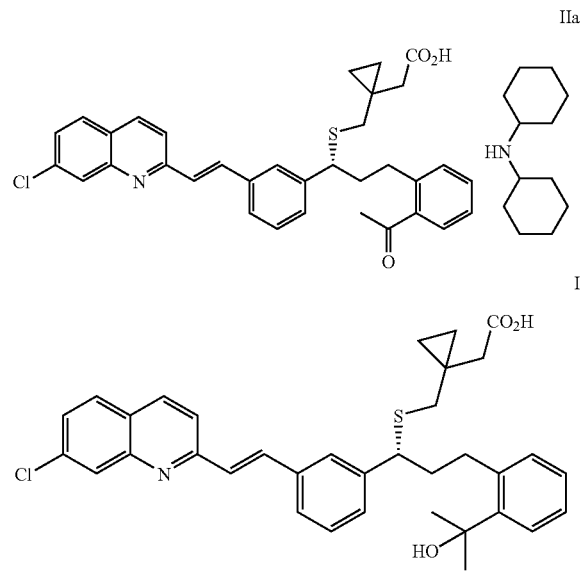

12 Claims, 1 Drawing Sheet

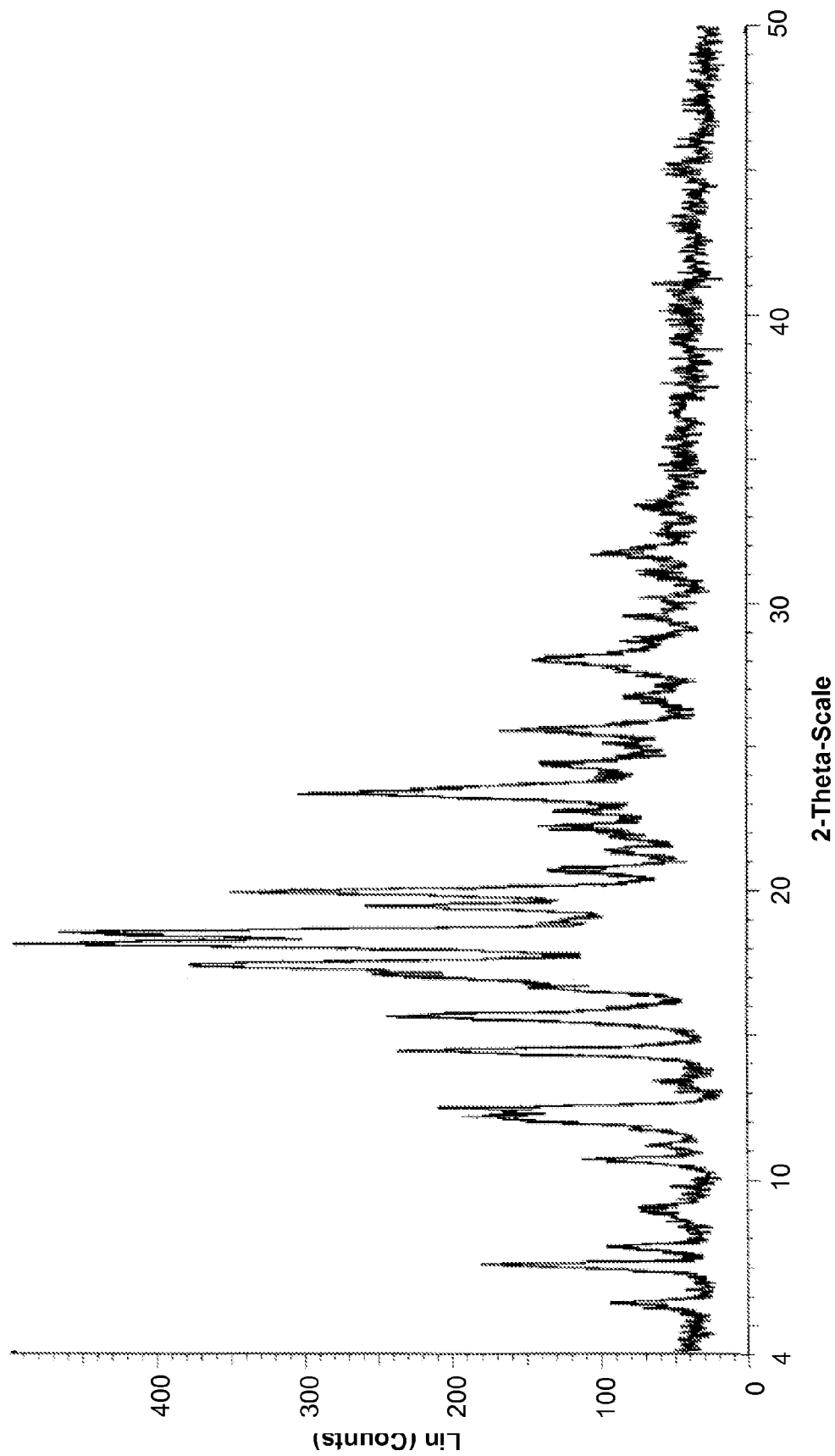

PROCESS FOR PREPARING A LEUKOTRIENE ANTAGONIST AND AN INTERMEDIATE THEREOF

CROSS-REFERENCE TO RELATED APPLICATIONS

This application is being filed under Rule 1.371 as a National Stage Application of pending International Application No. PCT/EP2008/059965 filed Jul. 30, 2008, which claims priority to parent application Spainsh Patent Application No. P 200702220, filed Jul. 31, 2007. Both International Application No. PCT/EP2008/059965 and Spanish Patent Application No. P 200702220 are hereby incorporated by reference herein in their entirety.

FIELD OF THE INVENTION

The present invention relates to a process for preparing montelukast, and novel intermediates used in such process.

BACKGROUND OF THE INVENTION

Montelukast is the International Non-proprietary Name (INN) for (R)-(E)-1-(((1-(3-(2-(7-chloro-2-quinolinyl)ethenyl)phenyl)-3-(2-(1-hydroxy-1-methylethyl)phenyl)propyl)thio)methyl)cyclopropane acetic acid, and CAS RN 158966-92-8.

Montelukast monosodium salt (CAS RN 151767-02-1) of formula Ia

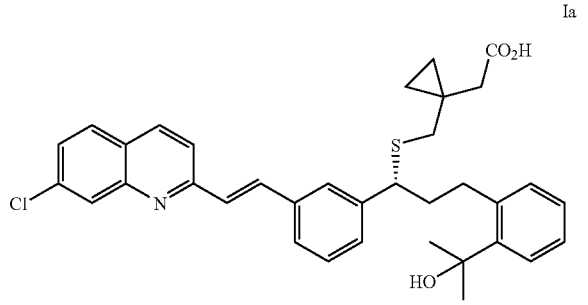

belongs to a group of drugs known as leukotriene antagonists. It is an orally active compound, which binds with high affinity and selectivity to CysLT1 receptor. Montelukast monosodium salt is currently used in the treatment of asthma, inflammation, angina, cerebral spasm, glomerular nephritis, hepatitis, endotoxemia, uveitis and allograft rejection.

The preparation of montelukast sodium salt was first described in EP 480717 (Example 161). Later on, an alternative process was described for the preparation of a montelukast intermediate in EP 500360. However, these processes are not particularly suitable for industrial-scale application due to the use of solvents such as dichloromethane, reagents such as hydrazine, and temperatures below −40° C. In addition, such processes require tedious chromatographic purifications of some intermediates and/or final products, and yields of final product are low.

Among the strategies for the preparation of montelukast, processes comprising the formation of amine salts of montelukast which are subsequently converted into its sodium salt have also been described. Some of these processes, as described below, comprise the purification of the dicyclohexylamine salt of montelukast:

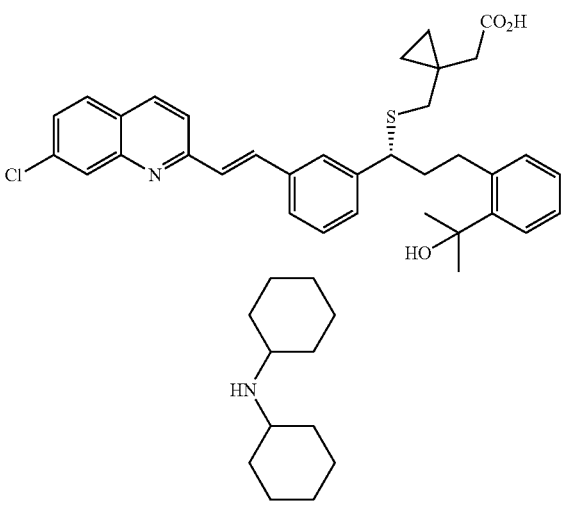

Thus, for example, European Patent Application EP 737186 (whose United States equivalent is U.S. Pat. No. 5,614,632), discloses a process to prepare a crystalline form of montelukast sodium from the dicyclohexylamine salt of montelukast. This process is hardly applicable on an industrial scale since a highly flammable base (n-butyl lithium) and reaction temperatures below −10° C. are used. In addition, an impurity, which is derived from dehydration of the tert-butanol group, is formed during the preparation of montelukast and its removal becomes very difficult. Moreover, the purification steps via the dicyclohexylamine salt are very time consuming and comprise seeding of montulekast and dicyclohexylamine solution in toluene or ethyl acetate, and subsequent addition of heptane or hexane respectively.

In document WO 06/008751 (whose United States equivalent is United States Publication No. 2009/143590), another process is described for obtaining montelukast sodium salt which comprises converting montelukast into its dicyclohexylamine salt. However, this process also requires seeding of the solution, and a very long period of time (more than one day) is needed for crystallization of the dicyclohexylamine salt.

Moreover, purification via the dicyclohexylamine salts has also been applied to intermediates which are subsequently converted into montelukast.

Thus, documents WO 06/008751 (whose United States equivalent is United States Publication No. 2009/143590), and WO 07/004237 describe the preparation of montelukast through the formation of a dicyclohexylamine salt of the methyl ester intermediate of formula:

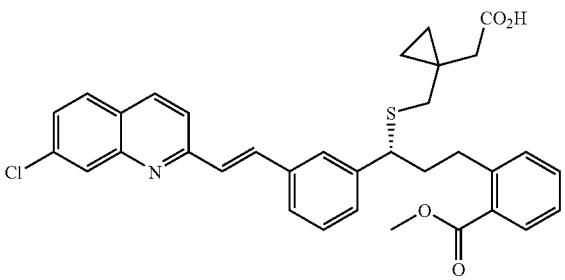

However, these processes show the same drawbacks as those described for the formation of dicyclohexylamine salts over montelukast acid.

Therefore, due to the difficulty in purifying montelukast and its intermediates, the provision of alternative processes for preparation of montelukast, it is of great interest, particularly if they are easily industrializable.

SUMMARY OF THE INVENTION

The inventors have found that the preparation of a dicyclohexylamine salt of formula IIa

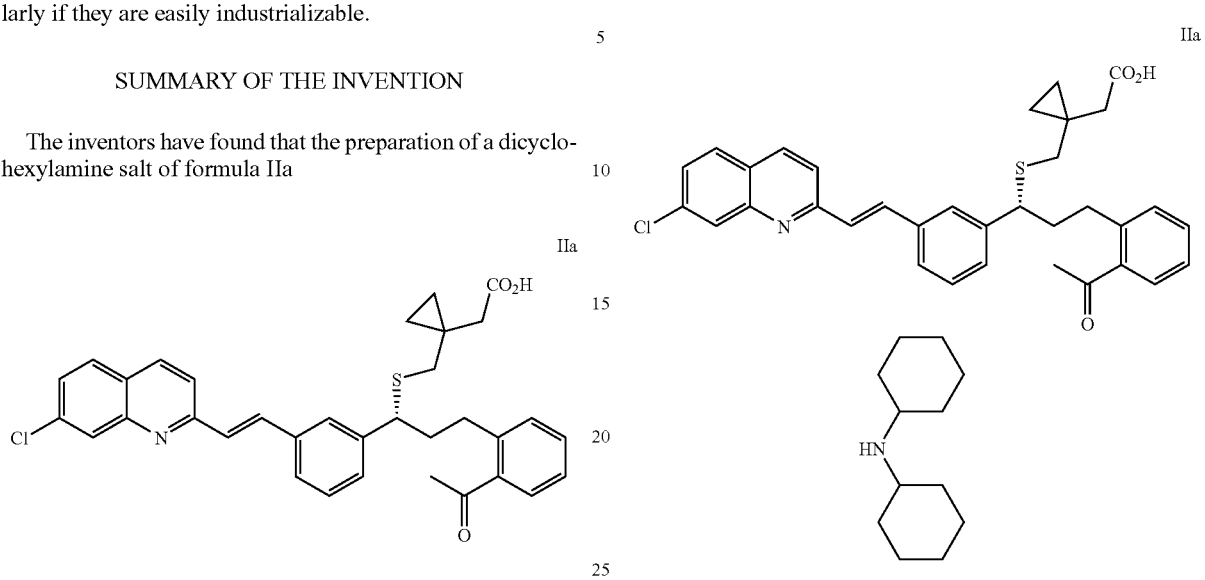

allows to obtain montelukast, as well as its salts and solvates, including hydrates, by an easily scalable process which overcomes the prior art drawbacks.

The dicyclohexylamine salt of formula IIa, as illustrated by the examples, is much more insoluble in polar solvents than the known dicyclohexylamine salts of montelukast and its methyl ester intermediate. Due to its different solubility, this salt shows the advantage of being easily crystallizable in said polar solvents, and the duration of salt formation becomes considerably shorter. Likewise, seeding of the solution to start crystallization is not necessary, which facilitates—in practice—the industrial-scale operating conditions since procedures that may be dangerous due to the flammability of such solvents are avoided. Additionally, the product is obtained in high yield and with a high purity.

Another advantage of the use of the salt of formula IIa is that it can be obtained by using polar solvents without the need for mixtures of non-polar solvents, which facilitates the isolation of the product. Furthermore, the use of one sole solvent for crystallization facilitates its recovery and reuse in an industrial process.

Moreover, if desired, purification of the salt of formula IIa may be carried out in the same solvent as that used for crystallization.

Therefore, a first aspect of the invention relates to a compound of formula IIa,

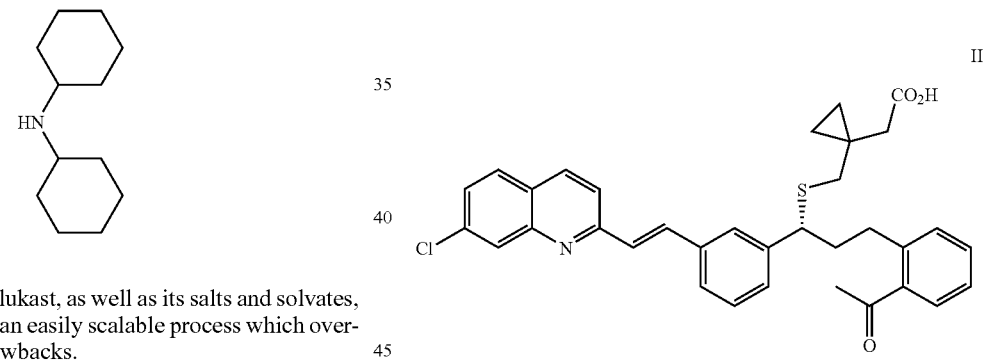

or a pharmaceutically acceptable solvate thereof, including a hydrate.

Another aspect of the invention relates to a process for the preparation of a compound of formula IIa as defined above, which comprises reaction of a compound of formula II

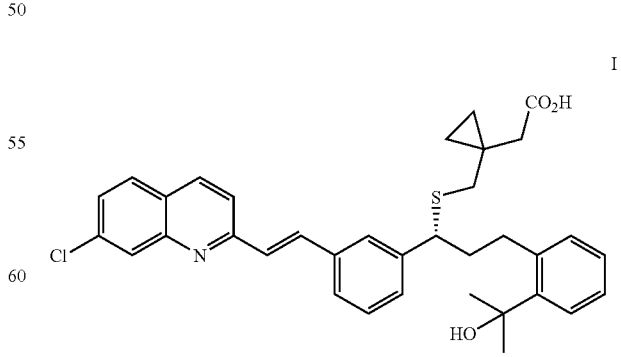

with dicyclohexylamine in the presence of a polar solvent.

Another aspect of the invention relates to a process for preparing a compound of formula I,

I or a pharmaceutically acceptable salt thereof, or a pharmaceutically acceptable solvate thereof, including a hydrate; which comprises conversion of a compound of formula IIa

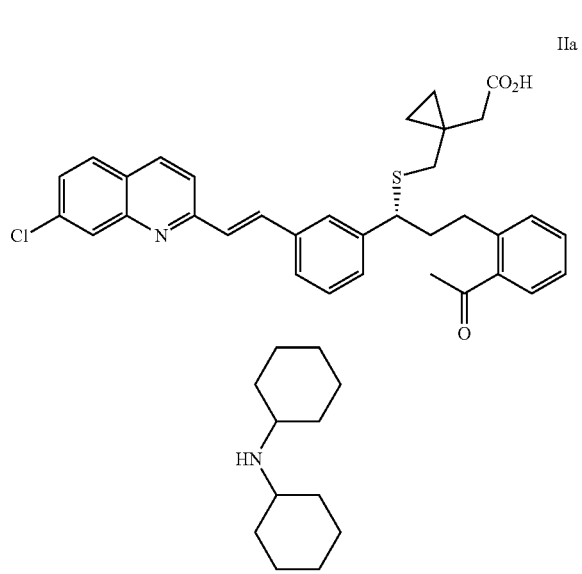

into a compound of formula II by aqueous treatment in an acid medium;

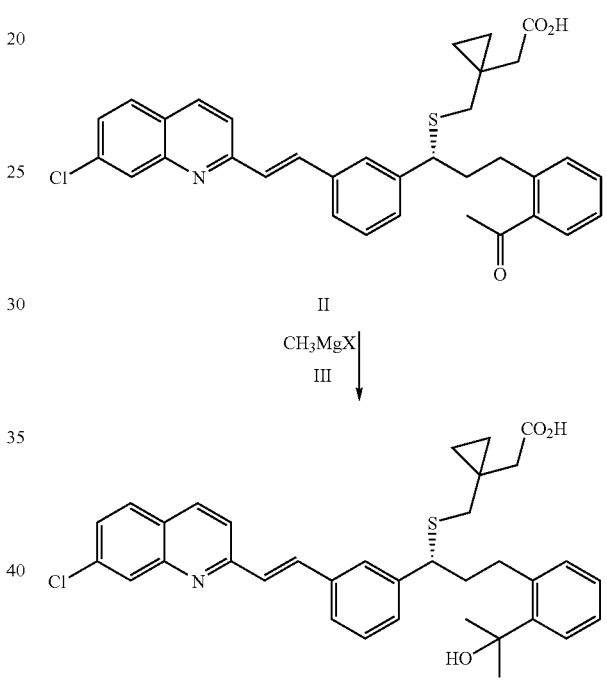

followed by reaction with a compound of formula III CH₃MgX, wherein X is halogen, optionally in the presence of a Lewis acid, in a suitable solvent; and subsequent aqueous treatment in an acid medium to give the compound of formula I; and, optionally, the compound of formula I is converted into a pharmaceutically acceptable salt thereof by treatment with the corresponding base, or a salt of the compound of formula I is converted into another salt of compound of formula I by ion exchange, or the compound of formula I is converted into a pharmaceutically acceptable solvate thereof, including a hydrate, by crystallization/precipitation in a suitable solvent.

BRIEF DESCRIPTION OF THE FIGURES

FIG. 1 depicts the X-ray diffractogram of the crystalline form of (R)-(E)-1- (((1-(3-(2-(7-chloro-2-quinolinyl)ethenyl)phenyl)-3-(2-acetylphenyl)propyl)thio) methyl)cyclopropane acetic acid dicyclohexylamine salt.

DETAILED DESCRIPTION OF ADVANTAGEOUS EMBODIMENTS OF THE INVENTION

Montelukast (compound of formula I) and its intermediates may be prepared by the processes hereinafter described. The most appropriate conditions under which the process is carried out may vary depending on different parameters considered by those skilled in the art, such as the concentration of starting material, temperature, solvent used and the like. These parameters may be easily determined by those skilled in the art through routine testing and using the teachings in the examples of the present specification.

In some reactions of the present invention, an aqueous treatment is utilized in an acid medium for isolation of the reaction product. Generally, said acid may be an organic acid. Examples or organic acids include, among others, acetic acid, methanesulfonic acid, trifluoromethanesulfonic acid, ethanesulfonic acid, benzenesulfonic acid or p-toluenesulfonic acid. In a particular embodiment the acid used is acetic acid.

As mentioned above, the compound of formula I may be prepared by reaction of a compound of formula II with a compound of formula III, wherein X is halogen, as depicted on the following scheme:

This reaction is optionally carried out in the presence of a Lewis acid in a suitable solvent, such us tetrahydrofuran, and at a suitable temperature, preferably at 0° C., and a subsequent aqueous treatment in an acid medium is performed to yield the compound of formula I.

Throughout the specification, the term Lewis acid is used herein to refer to a substance which can accept an electron pair. Examples of Lewis acids include, among others, AlCl₃, FeCl₃, ZnCl₂ and CeCl₃.

In a preferred embodiment, in the compound of formula III X is Cl and the reaction is carried out in the presence of a Lewis acid. In another preferred reaction, in the compound of formula III X is Cl and the Lewis acid is CeCl₃.

The compound of formula II is obtained by aqueous treatment of the salt of formula IIa in an acid medium, preferably in acetic acid, in a suitable solvent, such as a mixture of toluene and water, and at a suitable temperature, preferably room temperature.

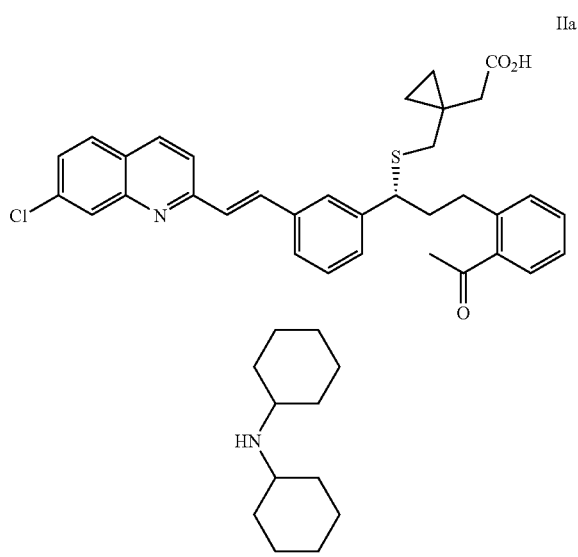

The process for preparing a compound of formula IIa comprises reaction of a compound of formula IV, wherein LG represents a leaving group selected from the group consisting of methanesulfonyloxyl and p-toluenesulfonyloxyl, with a compound of formula V, wherein R represents an alkaline metal, such as Na, Li or K, followed by treatment with dicyclohexylamine (DCHA) in a polar solvent, as depicted on the following synthetic scheme:

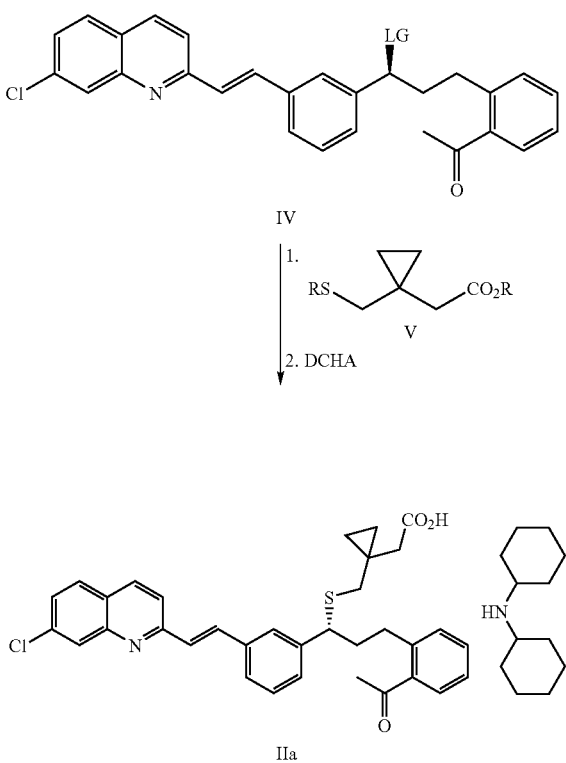

The first step is carried out preferably in a solvent system such as dimethylformamide, acetone and toluene, at room temperature. In a preferred embodiment LG represents methanesulfonyloxyl. In another preferred embodiment R represents Na.

The second step comprises reaction of the compound in free acid form, which is obtained in the first step after an aqueous treatment in an acid medium, with dicyclohexylamine to yield, within a few minutes and without the need for seeding, the salt of formula IIa. This reaction is carried out in a polar solvent.

The term polar solvent, as used in the present invention, refers to a solvent in whose molecules there is either a permanent separation of positive and negative charges, or the centres of positive and negative charges do not coincide. Examples of polar solvents include ketones; alcohols, such as isopropanol or ethanol; esters; halogenated hydrocarbons, such as chloroform or methylene chloride; ethers, such as isopropyl ether or methyl tert-butyl ether; and polar aromatic hydrocarbons.

The term aromatic hydrocarbon is used herein to refer to a mono- or di-substituted benzene, wherein the substituent is selected from halogen or methyl. Examples of aromatic hydrocarbons of the invention include toluene, xylene or chlorobenzene.

In a preferred embodiment, the polar solvent is selected from the group consisting of a ketone of formula $RCOR_1$, an ester of formula $RCO_2R_1$ and toluene; wherein R and $R_1$ may be the same or different and represent $(C_1-C_4)$alkyl.

The term $(C_1-C_4)$alkyl represents a saturated straight or branched hydrocarbon chain having from 1 to 4 carbon atoms. Examples include methyl, ethyl, propyl, isopropyl, butyl, isobutyl, sec-butyl and tert-buthyl groups. Thus, examples of ketones of formula $RCOR_1$ include, among others, acetone, methyl ethyl ketone, diethyl ketone or methylisobutylketone; and examples of esters of formula $RCO_2R_1$ include, among others, ethyl acetate or isopropyl acetate.

In a yet more preferred embodiment, the solvent is acetone, isopropyl acetate or toluene. In the most preferred embodiment the solvent is acetone. Preferably, crystallization is carried out at room temperature. If necessary, the obtained salt may be purified by using the same solvent.

Preferably, the compound of formula IIa thus obtained is in a crystalline form. In a particular embodiment, the compound of formula IIa thus obtained is the crystalline form of the (R)-(E)-1-(((1-(3-(2-(7-chloro-2-quinolinyl)ethenyl)phenyl)-3-(2-acetylphenyl)propyl)thio)methyl)cyclopropane acetic acid dicyclohexylamine salt, whose X-ray diffractogram is substantially the same as that shown in FIG. 1.

The compounds of formula V may be obtained from mercaptomethylcyclopropylacetic acid by reaction with a base, for example NaH, in a suitable solvent such as dimethylformamide, and preferably upon cooling.

The compounds of formula IV may be prepared in a two-step sequence. In the first step, the compound of formula VII is reacted with a compound of formula III wherein X is halogen, preferably chloro, to give, after aqueous treatment, a compound of formula VI. This reaction is carried out in the presence of lithium bis(trimethylsilyl)amide in a suitable solvent, such as a mixture of tetrahydrofuran and toluene, and at a suitable temperature, preferably upon cooling.

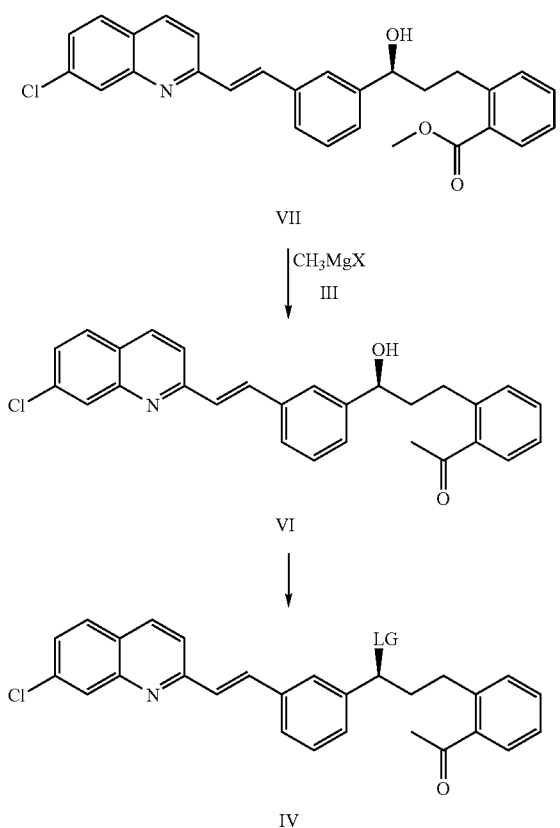

In the second step, the hydroxyl group of the compound of formula VI is converted into a leaving group selected from the group consisting of methanesulfonyloxyl and p-toluenesulfonyloxyl. In a preferred embodiment, LG represents methanesulfonyloxyl. This reaction is carried out in the presence of a sulfonyl halide, such as methanesulfonyl chloride or p-toluenesulfonyl chloride, in the presence of a base, such as pyridine or triethylamine, in a suitable solvent such as toluene, and at a suitable temperature, preferably upon cooling.

The compounds of formula IV, wherein LG is p-toluenesulfonyloxyl, are new and form also part of the invention.

The present invention also relates to salts of the compounds of formula I. A preferred embodiment relates to montelukast sodium salt of formula Ia. Said salt may be prepared from a compound of formula I or a salt thereof in the presence of NaOH in a suitable polar solvent, such as toluene or isopropyl acetate, by using a suitable non-polar solvent, such as n-heptane, to precipitate the product, and at an appropriate temperature, preferably at 15-20° C.

Throughout the specification and claims the term "comprising" and its variations are not meant to exclude other technical characteristics, additives, components or steps. Other objectives, advantages and characteristics of the invention will become apparent to those skilled in the art in part from the description and partly from the practice of the invention. The following examples are provided for illustrative purposes and are not meant to be limiting of the present invention

EXAMPLES $^1$H-NMR and $^{13}$C-NMR spectra were recorded at room temperature on a Mercury 400 MHz spectrometer.

HPLC spectra were recorded using a Waters Alliance 2695 system equipped with UV Waters 2487 detector.

X-ray diffractogram was obtained at room temperature using a Siemens D500 diffractometer equipped with a Cu anode ($\lambda$=1.54056 Å).

Example 1

(S)-(E)-1-(2-(1-(3-(2-(7-chloro-2-quinolinyl)ethenyl) phenyl)-hydroxypropyl)phenyl)ethanone monohydrate (VI)

To a 1M solution (390 ml) of lithium bis(trimethylsilyl) amide in tetrahydrofuran, 65 ml of a 3M solution of methylmagnesium chloride in tetrahydrofuran were slowly added under $N_2$ atmosphere at a temperature of 0° C. The solution obtained was maintained for 30 minutes at 0-5° C. under stirring. 25 g of methyl (S)-(E)-2-(3-(3-(2-(7-chloro-2-quinolinyl)ethenyl)phenyl)-hydroxypropyl) benzoate monohydrate (3.8% of water, VII, EP 480717, example 146, step 2) were dissolved in 250 ml of toluene. The solution was heated at reflux and water was separated by azeotropic disuntilation at a temperature above 110° C. The solution was concentrated to a volume of approximately 130 ml and the initially prepared reducing solution was slowly added under $N_2$ atmosphere at a temperature from 0° C. to −5° C. After the addition was completed, the reaction mixture was maintained for 15 hours under $N_2$ atmosphere at a temperature of 0-5° C.

The reaction mixture was added to an aqueous solution containing 400 ml of water, 75 g of sodium chloride, 70 ml of glacial acetic acid and 60 g of ammonium acetate, at a temperature below 25° C. The aqueous phase was separated and the organic phase was washed with two 100-ml portions of 5% aqueous sodium bicarbonate solution. The solvent from the resulting organic phase was removed by distillation under reduced pressure and the obtained residue was dissolved in 90 ml of acetone at 20° C. Then, 6 ml of water were added to afford a suspension. This suspension was maintained for 2 hours at a temperature of 15-20° C. and then filtered to afford a solid which was washed with methyl-tert-butylether. The isolated solid was dried at a temperature of 45-50° C. to afford 18.1 g of the title compound (99% purity by HPLC analysis and 74.0% yield).

$^1$H-NMR (400 MHz, CD$_3$OD): 1.97-2.03 (2H, m); 2.53 (3H, s); 2.80-2.98 (2H, m); 4.66-4.69 (1H, t); 7.24-7.45 (7H, m); 751-7.53 (1H, dt); 7.63 (1H, s); 7.68-7.72 (2H, m); 7.76-7.78 (1H, d); 7.78-7.80 (1H, d); 7.91-7.92 (1H, d); 8.18-8.20 (1H, d).

In this example, the enantiomeric excess of the starting compound VII was 96.5%, which led to compound VI with an enantiomeric excess higher than 99%, due to the precipitation of the latter in the mixture of acetone-water. When compound VI is obtained with an enantiomeric excess less than 99%, it may be purified by a recrystallization in 4 volumes of acetone and 0.5 volumes of water referred to the weight of compound VI. Thus, the solution obtained when heating the initial solution is cooled slowly to 15-20° C. in order to crystallize the product. The isolated solid by filtration shows an enantiomeric excess higher than 99.5%. This methodology avoids the dependency on the enantiomeric purity of the starting hydroxyester VII.

Example 2

(R)-(E)-1-(((1-(3-(2-(7-chloro-2-quinolinyl)ethenyl) phenyl)-3-(2-acetylphenyl)propyl)thio)methyl)cyclopropane acetic acid dicyclohexylamine salt (IIa)

a) (S)-(E)-1-(2-(1-(3-(2-(7-chloro-2-quinolinyl)ethenyl) phenyl)-1-(methanesulfonyl-oxy)propyl)phenyl)ethanone (IV.1)

20 g of the compound obtained in Example 1 (4% water, VI) were dissolved in 200 ml of toluene. The solution was heated at reflux and water was separated by azeotropic distillation. The solution was then concentrated to a volume of approximately 50 ml.

To the solution thus obtained, 8.4 g of triethylamine were added and the mixture was cooled to a temperature from −5 to −10° C. While maintaining this temperature, 7.1 g of mesyl chloride were slowly added and the mixture was stirred for 1 hour at the temperature from −5 to −10° C. under $N_2$ atmosphere. Thereafter, 200 ml of previously cooled acetone were added with stirring for 1 further hour at the temperature from 0 to −5° C. The solid present in the reaction mixture was separated by filtration and the resultant solution containing the mesyl derivative was kept at the temperature of −5° C.

b) Mercaptomethylcyclopropylacetic Acid Disodium Salt (V.1)

In a light-protected flask and under $N_2$ atmosphere, 4.4 g of 60% sodium hydride and 88 ml of dimethylformamide were mixed. To this mixture, a solution containing 8.1 g of mercaptomethylcyclopropylacetic acid and 20 ml of dimethylformamide was added while maintaining the temperature at 0-5° C. The reaction mixture was kept at this temperature for 1 hour.

c) Title Compound

Previous solution containing the mesyl derivative from step a) was quickly added to the suspension of mercaptomethylcyclopropylacetic acid disodium salt from step b) and the temperature was kept at 5-10° C. After the addition was completed, the temperature was adjusted to 20-25° C. and kept within this range for about 15 hours.

Then, the reaction mixture was cooled to 0-5° C. and 100 ml of an aqueous solution of sodium chloride were added. Acetone was removed by vacuum distillation and then 100 ml of isopropyl acetate were added. The aqueous phase was separated and the organic phase was washed with one 100-ml portion of aqueous sodium chloride solution. 100 ml of water were added and pH was adjusted to 4.5-5.5 with glacial acetic acid. The aqueous phase was separated and the solvent from the organic phase was removed by vacuum distillation, and the resulting residue was dissolved in 260 ml of acetone in a light-protected flask under $N_2$ atmosphere and the temperature was kept at 20-25° C. 7.9 g of dicyclohexylamine were obtained to afford within 5 minutes a white precipitate. The suspension was heated at reflux for 30 minutes. Then the suspension was cooled to 20-25° C. and kept within this temperature range for 2 hours. The resulting suspension was filtered off to give a white solid which was washed with acetone. The isolated solid was dried at the temperature of 45-50° C. to afford 24.6 g of the title compound (98.0% purity by HPLC analysis and 74.6% yield).

If necessary, the product thus obtained may be purified using a suspension in 15 volumes of acetone at reflux temperature. After cooling at a temperature of 20-25° C., the solid was filtered off to afford a product with 99.0% purity by HPLC analysis and a purification yield higher than 98%. The titled compound was obtained with an enantiomeric excess higher than 99.8%.

$^1$H-NMR (400 MHz, $CD_3OD$): 0.28-0.51 (4H, m); 1.15-1.39 (12H, m); 1.65-1.69 (2H, dd); 1.81-1.84 (4H, dd); 2.01-2.03 (4H, d); 2.11-2.15 (2H, m); 2.25-2.39 (2H, q); 2.46-2.50 (1H, d); 2.51 (3H, s); 2.60-2.63 (1H, d); 2.77-2.80 (1H, m); 2.88-2.90 (1H, m); 3.08-3.13 (2H, m); 3.90-3.94 (1H, t); 7.23-7.30 (2H, m); 7.35-7.42 (4H, m); 7.48-7.51 (1H, dd); 7.54-7.55 (1H, dd); 7.64 (1H, s); 7.70-7.72 (1H, dd); 7.76-7.80 (1H, d); 7.85-7.89 (2H, dd); 7.97-7.98 (1H, d); 8.26-8.28 (1H, d).

$^{13}$C-NMR (400 MHz, $CD_3OD$): 12.85, 13.31, 18.48, 25.54, 26.20, 29.93, 30.75, 33.42, 39.82, 41.01, 44.53, 50.86, 54.38, 120.90, 126.93, 127.24, 127.30, 127.97, 128.17, 128.32, 128.87, 130.05, 130.51, 130.55, 132.43, 132.74, 136.84, 137.40, 137.73, 138.17, 139.18, 142.74, 145.34, 149.38, 158.83, 180.30, 204.22.

Example 3

(R)-(E)-1-(((1-(3-(2-(7-chloro-2-quinolinyl)ethenyl) phenyl)-3-(2-(1-hydroxy-1-methylethyl)phenyl)propyl)thio)methyl)-cyclopropane acetic acid sodium salt (Montelukast sodium salt, Ia)

In a light-protected flask under $N_2$ atmosphere, 10 g of the compound obtained in Example 2, 100 ml of toluene and 50 ml of water were placed. 1 g of glacial acetic acid was added and the mixture was kept under stirring until obtaining a solution. The aqueous phase was separated and the organic phase was washed with two 50-ml portions of water. Water was removed from the resulting solution by azeotropic distillation and the solution was concentrated until obtaining a residue which was dissolved in 50 ml of tetrahydrofuran.

In parallel, a mixture of 2.9 g of anhydrous cerium (III) chloride and 50 ml of tetrahydrofuran was prepared and kept at reflux temperature for 1 hour. The mixture was then cooled to 0-5° C. and 17.5 ml of a 3M solution of methylmagnesium chloride in tetrahydrofuran was added while maintaining previous temperature range and under $N_2$ atmosphere. The resulting mixture was kept under stirring for 1 hour. Then, the previously prepared solution in tetrahydrofuran was slowly added at a temperature below 10° C. The reaction mixture was allowed to develop for 30 minutes at the temperature of 10-15° C. 56 ml of an aqueous solution containing 6 ml of glacial acetic acid and 50 ml of 10% aqueous acetic acid-sodium chloride solution were slowly added while maintaining the temperature below 20° C. After adding 100 ml of toluene, the aqueous phase was separated and the organic phase was washed with 100 ml of water. Water was removed from the resulting solution by azeotropic distillation and the solution was concentrated by distillation to afford a residue which was dissolved in 50 ml of anhydrous tetrahydrofuran.

Following the above described treatment, a mixture of 0.16 g of anhydrous cerium (III) chloride and 10 ml of a 3M solution of methylmagnesium chloride in tetrahydrofuran was prepared. The previously obtained tetrahydrofuran solution was slowly added and the temperature was kept below 10° C. The reaction mixture was allowed to develop for 30 minutes at the temperature of 10-15° C.

56 ml of an aqueous solution containing 6 ml of glacial acetic acid and 50 ml of 10% aqueous acetic acid-sodium chloride solution were slowly added while maintaining the temperature below 20° C. After adding 100 ml of toluene, the aqueous phase was separated and the organic phase was washed with 100 ml of water. Thereafter, the resulting organic phase was treated with an aqueous solution containing 1.75 g of 30% sodium hydroxide and 100 ml of a 20% aqueous sodium chloride solution. The aqueous phase was separated and the organic phase was repeatedly treated with two portions (100 and 50 ml) of water. To the combined aqueous phases, 100 ml of toluene and 30 g of sodium chloride were added, and the mixture was kept under stirring until complete dissolution of sodium chloride. The aqueous phase was separated and tetrahydrofuran and water were removed by azeotropic distillation. The solution obtained was treated with 0.5 g active charcoal. After filtration, the resulting solution was concentrated and the residue obtained was added to 50 ml of n-heptane at the temperature of 20° C. The resulting mixture was concentrated by distillation and 35 ml of n-heptane were added. The resulting mixture was kept under stirring for 2 hours at the temperature of 15-20° C. Finally, the precipitated solid was filtered off, washed with n-heptane and dried at the temperature of 60-80° C., to yield 6.4 g of amorphous solid form of montelukast sodium salt (>99.0% purity by HPLC analysis, 81.0% yield). The title compound was obtained with an enantiomeric excess higher than 99.8%.

Example 4

Comparison Among Crystallization Procedures of Dicyclohexylamine Salt

Comparison of crystallization procedures among montelukast dicyclohexylamine salt and methyl ester intermediate (as described in prior art) and the compound of the invention IIa is shown in Table 1.

Table 1 illustrates the starting material from which the dicyclohexylamine salt is formed, and crystallization conditions: solvent, time and if seeding is necessary. In all cases, temperature is 20-25° C.

TABLE 1

| Example | Solvent | Time | Seeding |
|---|---|---|---|
| R = —C(OH)(CH$_3$)$_2$ Ex. 3 (WO 06/08751) | Ethyl acetate/hexane | 24 h + 24 h | Yes |
| R = —C(OH)(CH$_3$)$_2$ Ex. 6 (WO 06/08751) | Ethyl acetate/hexane | 24 h + 24 h | Yes |
| R = —C(OH)(CH$_3$)$_2$ Ex. 7 (EP 737186) | Ethyl acetate/hexane | overnight | Yes |
| R = —C(OH)(CH$_3$)$_2$ Ex. 13 (EP 737186) | Toluene/heptane | overnight | Yes |
| R = —CO$_2$CH$_3$ E. 1 (WO 07/04237) | Ethyl acetate/hexane | 24 h + 24 h | Yes |
| R = —CO$_2$CH$_3$ Ex. 1 (WO 06/08751) | Ethyl acetate/hexane | 36 h + 24 h | Yes |
| R = —COCH$_3$ IIa | Acetone | 2 h | No |

It has been observed that unlike prior art compounds which even require the addition of large quantities of non-polar solvents to perform crystallization, the dicyclohexylamine salt of the compound of the invention IIa was obtained much more readily under the same temperature and without the need for addition of non-polar solvents.

Example 5

Solubility of Dicyclohexylamine Salts

Comparative solubilities of montelukast dicyclohexylamine salts, the methyl ester intermediate and the compound of the invention IIa are shown in Table 2. In particular, the amounts of solvents needed to dissolve each compound at reflux are provided.

The amounts of solvents needed to dissolve the salts are approximate. These amounts might slightly change depending on the quantity and purity of product or whether a crystalline or amorphous form is used. In the present example, the solubility of the same quantity of each compound was tested, and their purities were substantially similar. The results obtained show that the difference in solubility of the compound of the invention IIa in contrast to that of prior art compounds is significant.

TABLE 2

| Compound | Solvent |
|---|---|
| R = —C(OH)(CH$_3$)$_2$ | 10 volumes acetone |
| R = —CO$_2$CH$_3$ | 50 volumes acetone |
|  | 20 volumes isopropyl acetate |
| R = —COCH$_3$ (IIa) | 100 volumes acetone |
|  | 45 volumes isopropyl acetate |

The invention claimed is:

1. A process for the preparation of a compound of formula IIa

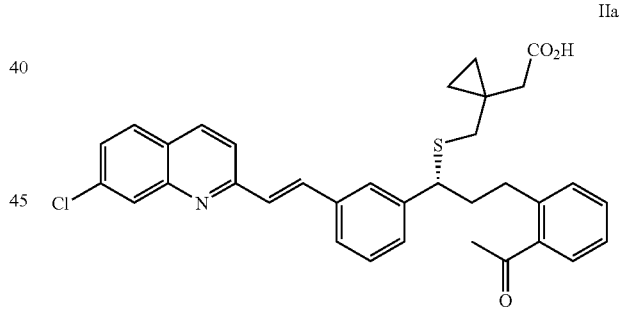

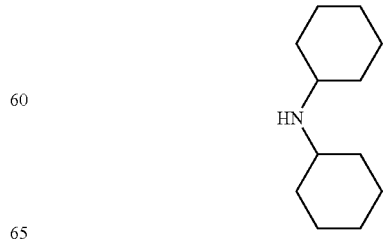

comprising reacting a compound of formula II

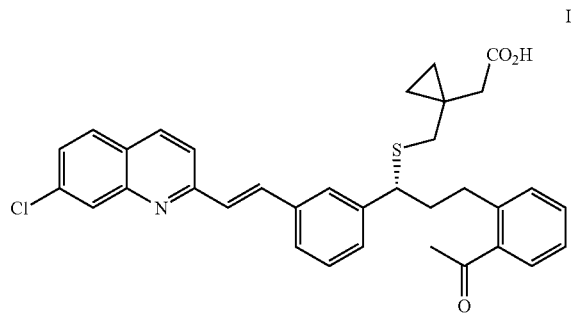

with dicyclohexylamine in the presence of a polar solvent.

2. The process of preparation according to claim 1, wherein the polar solvent is selected from the group consisting of a ketone of formula $RCOR_1$, an ester of formula $RCO_2R_1$ wherein R and $R_1$ may be the same or different and are $(C_1-C_4)$alkyl, and an aromatic hydrocarbon which is a mono or disubstituted benzene, wherein the substituent is selected from halogen or methyl.

3. The process of preparation according to claim 2, wherein the polar solvent is acetone.

4. The process of preparation according to claim 1, said process further comprising having previously reacted a compound of formula IV

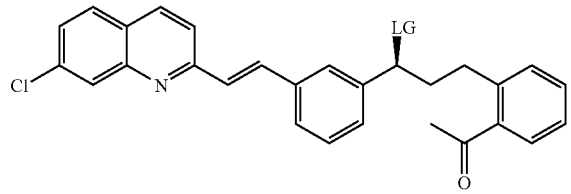

wherein LG represents a leaving group selected from the group consisting of methanesulfonyloxyl and p-toluenesulfonyloxyl;
with a compound of formula V

wherein R represents an alkaline metal, in a suitable solvent, followed by aqueous treatment in an acid medium, to afford the compounds of formula II.

5. The process of preparation according to claim 4, wherein LG represents methanesulfonyloxyl.

6. The process of preparation according to claim 4, wherein R represents Na.

7. A process for the preparation of a compound of formula I,

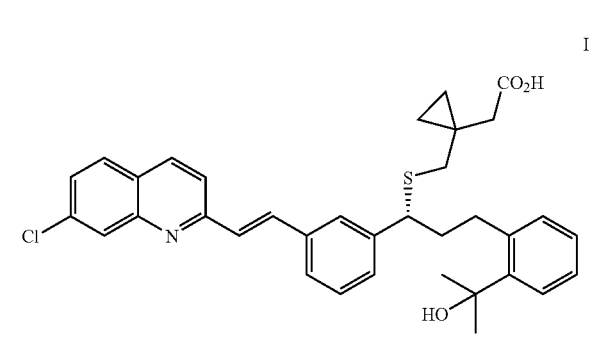

or a pharmaceutically acceptable salt thereof; comprising converting a compound of formula IIa

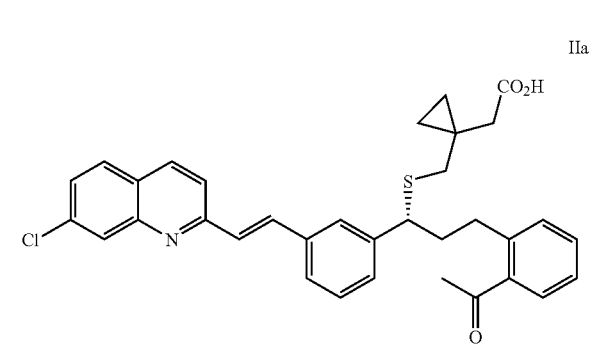

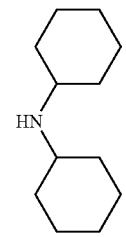

into a compound of formula II by aqueous treatment in an acid medium;

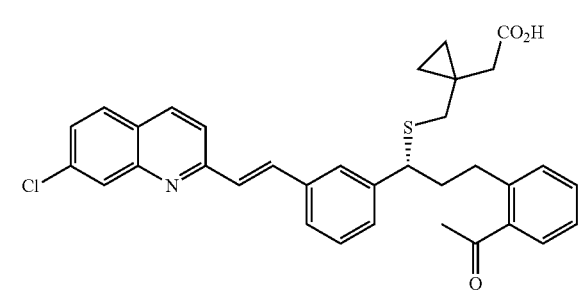

followed by reaction with a compound of formula III $CH_3MgX$, wherein X is halogen, in a suitable solvent, optionally in the presence of a Lewis acid; and subsequently performing an aqueous treatment in an acid medium to afford the compound of formula I; and, optionally, converting the compound of formula I into a pharmaceutically acceptable salt thereof by treatment with the corresponding base, or converting a salt of the compound of formula I into another salt of the compound of formula I by ion exchange.

8. A process of preparation according to claim 7, wherein X is Cl in the presence of a Lewis acid.

9. A process of preparation according to claim 8, wherein the Lewis acid is $CeCl_3$.

10. A process of preparation according to claim 7, said process further comprising having previously reacted a compound of formula II

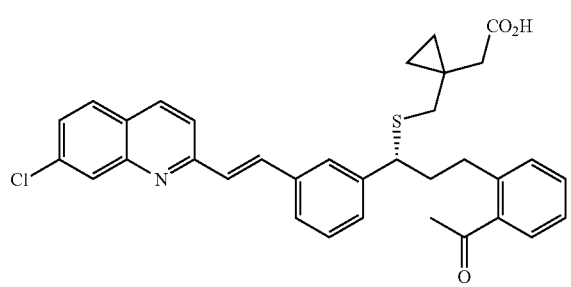

II with dicyclohexylamine in the presence of a polar solvent to afford a compound of formula IIa.

11. A process of preparation according to claim 10, said process further comprising having previously reacted a compound of formula IV

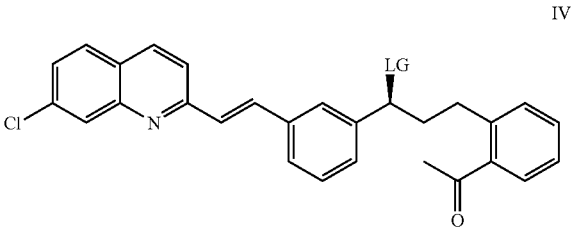

IV wherein LG represents a leaving group selected from the group consisting of methanesulfonyloxyl and p-toluenesulfonyloxyl,
with a compound of formula V

V wherein R represents an alkaline metal, in a suitable solvent, followed by aqueous treatment in an acid medium, to afford the compound of formula II.

12. A process of preparation according to claim 5, wherein R represents Na.

* * * * *